United States Patent
Boutoussov et al.

(10) Patent No.: US 8,403,922 B2
(45) Date of Patent: Mar. 26, 2013

(54) NON-CONTACT HANDPIECE FOR LASER TISSUE CUTTING

(75) Inventors: Dmitri Boutoussov, Dana Point, CA (US); Manvel Andriasyan, San Diego, CA (US)

(73) Assignee: Biolase, Inc., Irvine, CA (US)

( * ) Notice: Subject to any disclaimer, the term of this patent is extended or adjusted under 35 U.S.C. 154(b) by 617 days.

(21) Appl. No.: 12/626,271

(22) Filed: Nov. 25, 2009

(65) Prior Publication Data

US 2010/0137852 A1 Jun. 3, 2010

Related U.S. Application Data

(60) Provisional application No. 61/156,440, filed on Feb. 27, 2009, provisional application No. 61/118,609, filed on Nov. 29, 2008.

(51) Int. Cl.
*A61B 18/18* (2006.01)

(52) U.S. Cl. .................. 606/18; 606/17; 606/13; 606/2; 607/89; 607/93

(58) Field of Classification Search .................. 606/18, 606/17, 13, 2; 607/89, 93
See application file for complete search history.

(56) References Cited

U.S. PATENT DOCUMENTS

| | | | |
|---|---|---|---|
| 5,125,923 A | 6/1992 | Tanner et al. | |
| 5,370,643 A * | 12/1994 | Krivoshlykov et al. | 606/16 |
| 5,374,266 A | 12/1994 | Kataoka et al. | |
| 5,971,755 A | 10/1999 | Liebermann et al. | |
| 6,190,376 B1 | 2/2001 | Asah et al. | |
| 7,187,822 B2 | 3/2007 | Rizoiu et al. | |
| 2003/0228094 A1* | 12/2003 | Rizoiu et al. | 385/25 |
| 2006/0095096 A1* | 5/2006 | DeBenedictis et al. | 607/88 |
| 2006/0129141 A1 | 6/2006 | Lin | |
| 2007/0100401 A1* | 5/2007 | Lin | 607/89 |
| 2007/0190482 A1 | 8/2007 | Rizoiu | |

FOREIGN PATENT DOCUMENTS

| | | |
|---|---|---|
| DE | 3800555 A1 | 7/1989 |
| EP | 0336045 A1 | 10/1989 |

OTHER PUBLICATIONS

International Search Report and Written Opinion, PCT/US09/65950, mailed Apr. 28, 2010.
Supplementary European Search Report, EP 09829802, mailed May 8, 2012.

* cited by examiner

*Primary Examiner* — Kinam Park
(74) *Attorney, Agent, or Firm* — Jones Day

(57) ABSTRACT

A non-contact laser handpiece contains optical components modified to provide a high-density uniform laser beam at a distance from the handpiece that minimizes effects of back reflection.

9 Claims, 3 Drawing Sheets

NON-CONTACT HANDPIECE FOR LASER TISSUE CUTTING

CROSS-REFERENCE TO RELATED APPLICATIONS

This application claims the benefit of U.S. Provisional Application No. 61/156,440, filed Feb. 27, 2009 and U.S. Provisional Application No. 61/118,609, filed Nov. 29, 2008, the entire contents of both which are hereby incorporated by reference.

BACKGROUND OF THE INVENTION

1. Field of the Invention

The present invention relates generally to a laser treatment (e.g., cutting) device for treating (e.g., cutting) hard and/or soft materials and, more particularly, to a laser delivery system for supplying components to the laser treatment device.

2. Description of Related Art

A conventional medical handpiece comprises a waveguide (e.g., a fiber optic or trunk fiber) connected to a laser housing or module that provides electromagnetic (e.g., laser) energy that can be directed to a target surface such as bone or dental tissue by the handpiece in order to accomplish cutting of the tissue. FIG. 1 illustrates a prior-art handpiece 100 comprising a waveguide 105 that receives laser energy from the laser housing. The energy is transmitted through a window 110 and is reflected from a 90-degree mirror 115. Energy reflected from the mirror 115 is directed to a tip or ferrule 120 that directs the laser energy to the target surface.

FIGS. 2 and 3 illustrate isolated elements of handpieces generally similar to that of FIG. 1 and demonstrate representative prior-art designs of laser handpieces. FIG. 2 illustrates a device 200 comprising a waveguide 205 that emits laser energy and a flat window 210 through which the laser energy 212 is transmitted before reaching a concave reflector 215. Laser energy 217 reflected from the reflector 215 enters a tip 220 whence laser energy 222 output from the tip 220 may be directed to a target surface. Disadvantageously, the device 200 illustrated in FIG. 2 exhibits a diverging (e.g., spreading) of the laser energy 212 leaving the window 210. To the extent the concave reflector 215 may mitigate an effect of the spreading laser energy 212 by focusing the laser energy 217 entering the tip 220, such compensation in the example still does not provide an adequate net correction, as the tip 220 in the example continues to emit diverging laser energy 222.

Considering FIG. 3, it illustrates a prior-art device 300 comprising a waveguide 305 and a convex lens 310 that may reduce a diverging effect of laser energy 307 at the pre-reflector stage, directing laser energy 312 onto a flat reflector 315 from which laser energy 317 is directed through a flat window or tip 320 thereby producing laser energy 322 that can be focused onto a target, typically a few millimeters in front of the window 320.

In operation, each of the devices illustrated in FIGS. 1-3 is typically disposed very near, or even touching, the target surface owing to a shape and/or distribution of the electromagnetic laser energy emitted from an emitting surface of the device. Accordingly, back reflection of components from the target including, for example, fluids, particles, debris, energy (e.g., pressure waves), power-beam and/or visible light can reach the emitting surface, thereby degrading performance of the laser device.

A need thus exists in the prior art for a design architecture of a medical laser handpiece that can attenuate or eliminate the mentioned performance degradation, and enhance a speed of cutting (e.g., provide high speed cutting) of biological tissue relative to the mentioned constructions. A further need exists for a more reliable system for delivering electromagnetic energy to a target surface at a distance (e.g., a distance greater than required by the mentioned conventional devices) from an emitting surface that minimizes, reduces and/or eliminates harmful and/or undesirable (e.g., user detectable and/or device degrading) back reflection.

SUMMARY OF THE INVENTION

The present invention addresses these needs by providing, according to an embodiment, a handpiece for laser tissue cutting comprising a window that receives electromagnetic energy, and a reflector that redirects the electromagnetic energy received from the window to a tip, the tip directing the electromagnetic energy received from the reflector to a target surface (e.g., or other chosen vicinity, such as an "interaction zone" defined in the below-referenced U.S. Pat. No. 5,574,247) at a distance (e.g., a selected distance) from an emitting surface of the tip. The selected distance may be chosen to reduce back reflection of components from the target to the emitting surface to, near to, or below a level that negligibly impedes tissue cutting. An implementation of the invention herein disclosed focuses the electromagnetic energy directed to the target surface at the selected distance. According to an aspect of the invention, one or more of the window, reflector, and tip may be adapted to provide a desired distribution of electromagnetic energy at the target surface (e.g., or other chosen vicinity). According to another aspect of the invention, one or more of the window, reflector, and tip may be adapted to provide a desired disruption, as a consequence of, inter alias, the electromagnetic energy at the target surface.

The emitting surface of an embodiment of the invention exhibits at least in part, and typically all of, the functionality of a converging lens.

An embodiment of the handpiece may comprise a fluid output adapted to emit fluid particles, whereby electromagnetic energy emitted from the emitting imparts energy into the fluid particles to thereby apply disruptive forces to the target surface. Another embodiment of the invention includes a beam guide adapted to facilitate spacing of the tip from the target surface.

While the apparatus and method has or will be described for the sake of grammatical fluidity with functional explanations, it is to be expressly understood that the claims, unless indicated otherwise, are not to be construed as limited in any way by the construction of "means" or "steps" limitations, but are to be accorded the full scope of the meaning and equivalents of the definition provided by the claims under the judicial doctrine of equivalents.

Any feature or combination of features described or referenced herein are included within the scope of the present invention provided that the features included in any such combination are not mutually inconsistent as will be apparent from the context, this specification, and the knowledge of one skilled in the art. In addition, any feature or combination of features described or referenced may be specifically excluded from any embodiment of the present invention. For purposes of summarizing the present invention, certain aspects, advantages and novel features of the present invention are described or referenced. Of course, it is to be understood that not necessarily all such aspects, advantages or features will be embodied in any particular implementation of the present

DETAILED DESCRIPTION OF THE INVENTION

Figure 1:
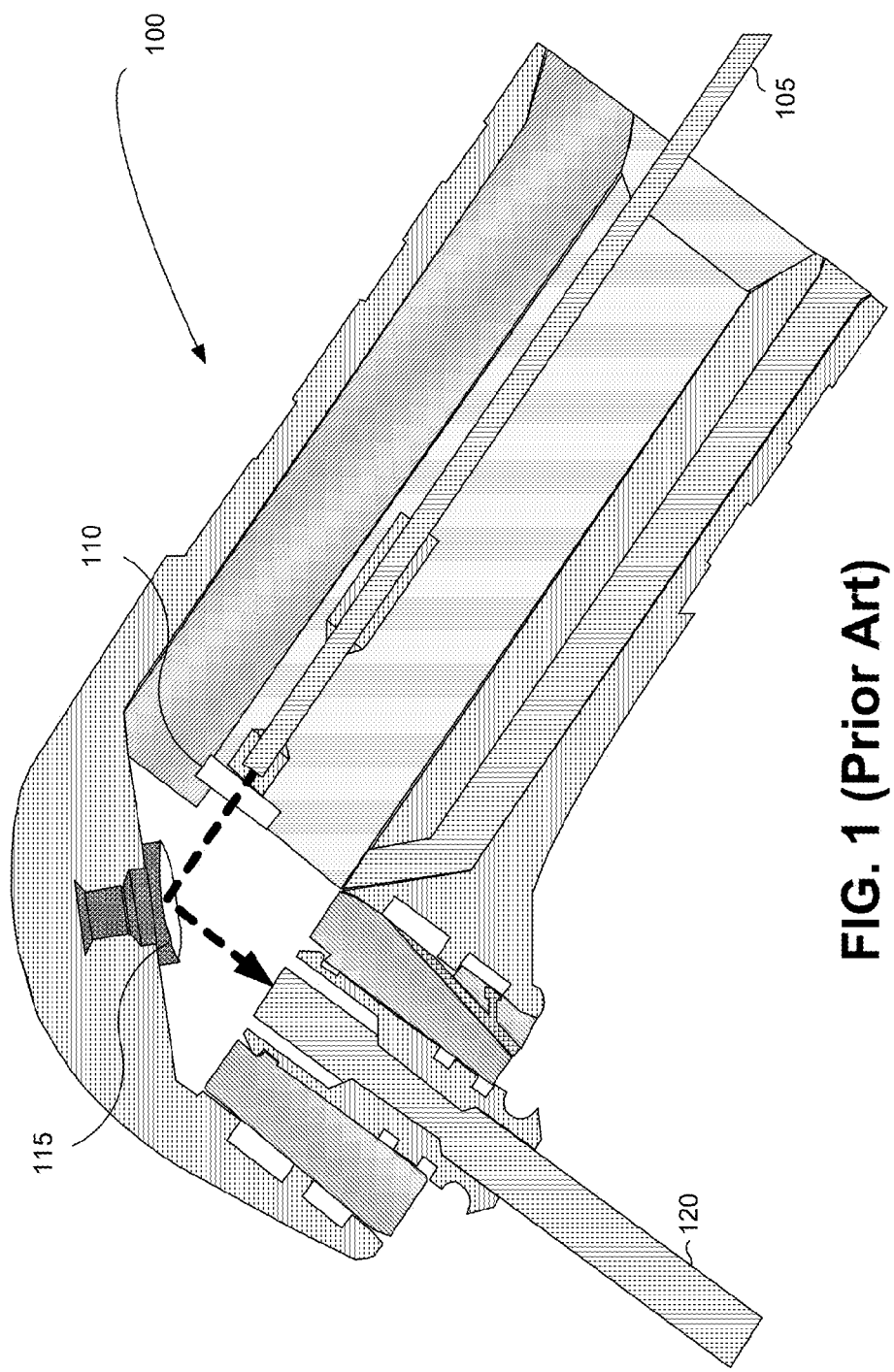
FIG. 1 is a diagram of a prior-art laser handpiece.

Embodiments of the invention are now described and illustrated in the accompanying drawings, instances of which are to be interpreted to be to scale in some implementations while in other implementations, for each instance, not. In certain aspects, use of like or the same reference designators in the drawings and description refers to the same, similar or analogous components and/or elements, while according to other implementations the same use should not. According to certain implementations, use of directional terms, such as, top, bottom, left, right, up, down, over, above, below, beneath, rear, and front, are to be construed literally, while in other implementations the same use should not. The present invention may be practiced in conjunction with various devices and techniques that are conventionally used in the art, and only so much of the commonly practiced process steps are included herein as are necessary to provide an understanding of the present invention. The present invention has applicability in the field of laser devices and processes in general. For illustrative purposes, however, the following description pertains to a laser cutting device.

Figure 4:
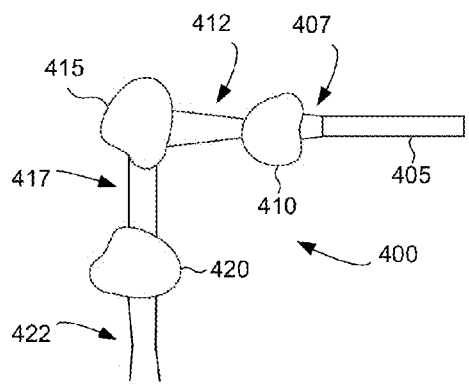
FIG. 4 is a schematic diagram of components of a laser handpiece according to the present invention.

With reference to FIG. 4, depicted therein is a schematic diagram of components of a laser handpiece 400 according to the present invention comprising a waveguide 405, which may be, for example, an optical fiber, that receives electromagnetic energy (e.g., laser energy) from a laser source (not shown). A laser beam 407, which comprises electromagnetic energy, may be emitted from the waveguide 405. A window 410 may receive the laser beam 407 and may or may not shape the beam 407 into a modified laser beam 412 that impinges on a reflector 415. The reflector 415 may further modify the laser beam 412 to produce another laser beam 417 that is coupled to a tip 420.

According to a feature of the present invention, the tip 420 modifies the laser beam 417. According to a further feature of the present invention, the tip 420, which typically may have a nominally cylindrical shape (but is not limited to such), operates as a lens to modify the laser beam 417. According to yet another feature of the present invention, the tip 420 converges the laser beam 417.

In the illustrated example, the tip 420 emits a laser beam 422 having a minimum cross-sectional width or "waist" (cf. portion of laser beam 22 indicated by arrowhead tip of lead line 422). The part of laser beam 422 shown with the smallest cross-sectional width corresponds to the focal point or peak-concentration part of the laser beam 422, and may be directed to a target surface to accomplish relatively high-power or focused cutting of, for example, tissue.

Figure 2:
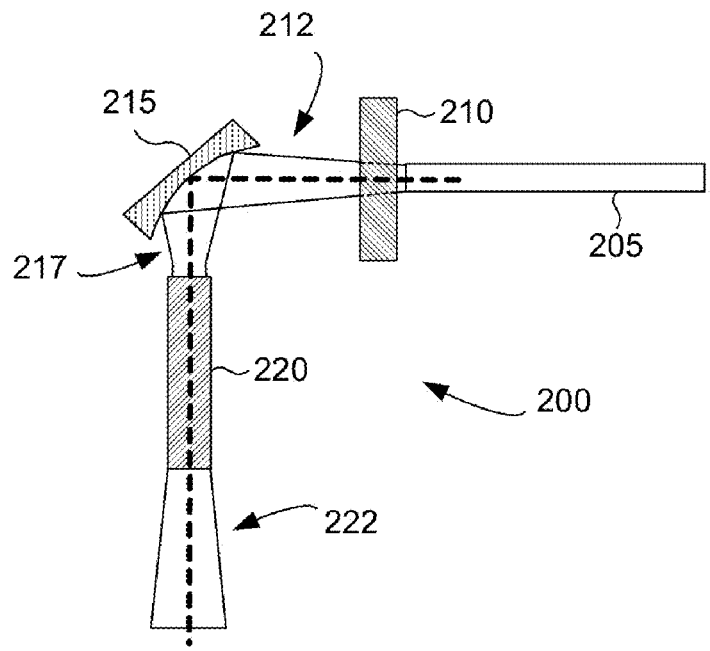
FIG. 2 is a schematic diagram of components of an example of a prior-art laser handpiece.
Figure 3:
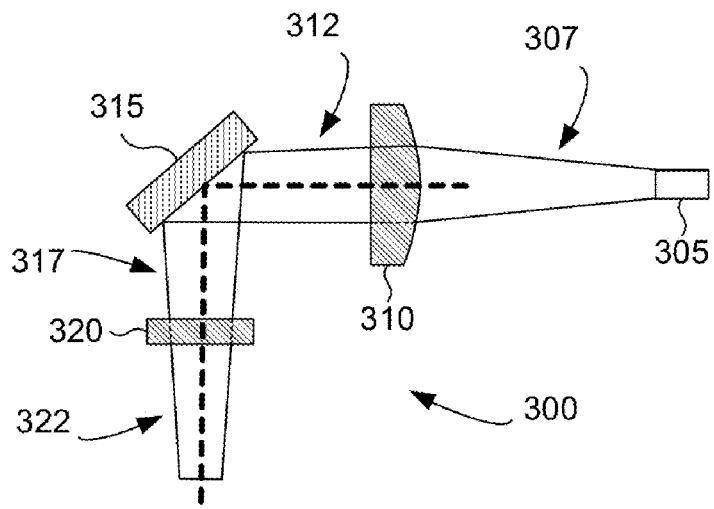
FIG. 3 is a schematic diagram of components of another example of a prior-art laser handpiece.
Figure 5A:
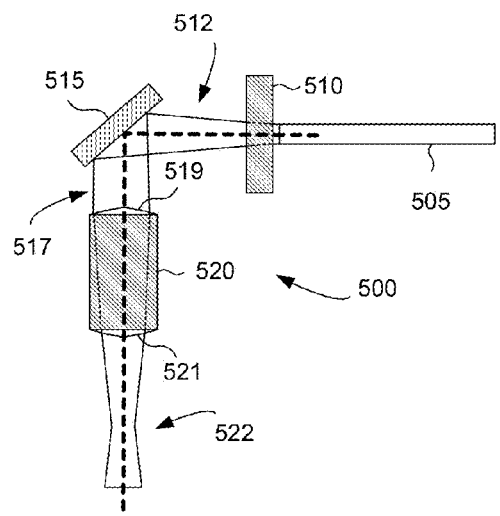
FIG. 5A is a schematic diagram of an embodiment of a laser handpiece architecture designed according to the present invention.

Many variations on the theme of the conceptual embodiment 400 may be designed by changing parameters of one or more of the window 410, the reflector 415, and the tip 420. FIG. 5A is a schematic diagram of one embodiment of a laser handpiece designed according to the present invention. The illustrated embodiment comprises a waveguide 505 that may provide functionality as described supra with reference to the waveguide 405 in FIG. 4. The window 410 in the embodiment of FIG. 4 may be implemented as a window 510 in the embodiment of FIG. 5A. The window 510 may be formed of, for example, sapphire or glass transparent optical material, may or may not have an antireflective (AR) coating, and may be flat or lensed. Similarly, the reflector 415 in FIG. 4 may be implemented as a reflector 515 in the embodiment of FIG. 5A. The reflector 515 (e.g., a mirror) may be formed of, for example, metal, ceramic material, sapphire, gold or other highly reflective (HR) material coated or plated for maximum reflection. Exemplary shapes of the reflector 515 may include flat, toroidal, parabolic, and the like. For instance, in modified embodiments the reflector may resemble either of those shown in FIG. 1 or 2.

The tip 420 of FIG. 4 may be implemented as a tip 520 (that may be, for instance, a window) formed, for example, as a nominally cylindrical structure of, for example, one or more of sapphire and low OH glass. A typical tip 520 may be (but is not limited to) a non-coated construction, and/or may have biconvex shapes 519 and 521 as illustrated. Representative dimensions of the tip 520 may include a length ranging from about 2 mm to about 5 mm with a diameter ranging from about 1 mm to about 3 mm.

Figure 5B:
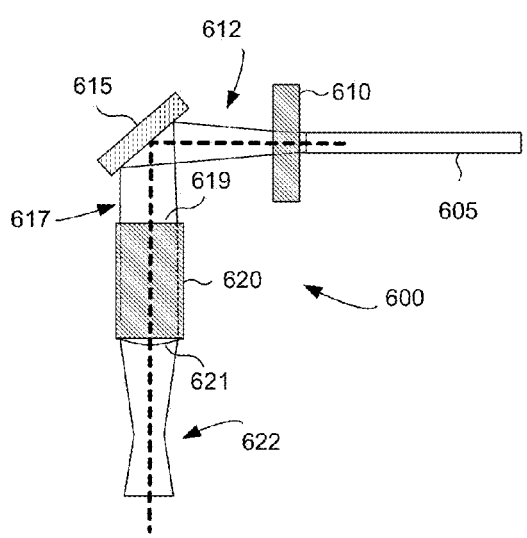
FIG. 5B is a schematic diagram of components of another laser handpiece embodiment designed according to the present invention.

FIG. 5B illustrates another variation on the theme of FIG. 4, the embodiment of FIG. 4 being similar the embodiment of FIG. 5B with elements that evidently correspond to those of the embodiment of FIG. 4. The embodiment of FIG. 5B differs in that a single convex surface 621 is provided on an output of a tip 620, the input to the tip being implemented as a flat surface 619.

With continuing reference to the embodiments illustrated in FIGS. 5A and 5B, the embodiments may generate output laser beams 522 and 622 that exhibit a minimum width portion or "waist" that can be designed to have specified dimensions (e.g., a distance from the tip 520/620 and/or a beam diameter at the waist) according to shapes and/or materials chosen for one or more of the window 510/610, the reflector 515/615, and the tip 520/620 in respective FIGS. 5A and 5B.

Control of parameters of the waist can allow an improvement in high speed cutting of biological tissues (e.g., soft tissue, hard tissue, bone and/or hard tooth tissue) as compared with prior-art laser handpieces. Significantly increased reliability of the illustrated delivery systems (e.g., handpieces 500/600) due to an attenuation or complete absence of contact (e.g., direct contact), between the tip 521/621 (e.g., the emitting surface 521/621 of the tip) and target tissue, whereby, for example, a relatively long distance (e.g., 5 or more, or, alternatively, 6 to 10 mm), between the output-tip emitting surface and the cutting tissue plane (i.e., between the emitting surface and the waist), can be created. For instance, a relatively great distance (e.g., more than 5 mm), between the output-tip emitting surface and the cutting tissue plane, can advantageously or substantially reduce an amount of back reflection of, e.g., the power beam, back into the fiber emitting surface.

One or more of these described effects on the beam path can be achieved by way of the new design of optical element (s) within the handpiece as described herein. The design(s) of this invention target the achievement of one or more of high density and uniformity (i.e., an about uniform cross-section) of electromagnetic energy (e.g., laser) power at a selected and controlled distance from output tip emitting surface. Another feature of the present invention is to increase depth (e.g., to the target surface), wherein laser high-power density is kept relatively consistent at the increased depth.

Inventive designs of laser handpieces according to an aspect of the invention utilize converging-beam shapes and/or functions at or adjacent to the emitting surface of the output tip. Thus, the present invention incorporates a modification of the shape of the emitting surface. Inventive designs of laser handpieces additionally and/or alternatively, may modify one, more than one, or all, of the other surfaces of the three optical elements (window, mirror and tip) to achieve, modify, control, and/or enhance the converging-beam function. In all, or at least certain, combination(s), the interrelation of the surfaces operate to achieve rapid, non-contact (i.e., without direct contact between the output tip and tissue, or with increased-spacing) cutting. According to a contemplated configuration, a relatively long distance (e.g., 5 or more mm) can be maintained between the emitting surface of the output tip and the cutting tissue plane, thereby measurably, substantially, advantageously, and/or dramatically reducing the effect of back reflection of components (e.g., fluids, particles, debris, energy, power-beam and/or visible light) to or into emitting surface(s), the reflection of which may impede tissue cutting.

According to one or more features of the invention, an output tip is provided with an emitting surface that resembles and/or replicates a shape and/or functionality of a lens (e.g., that has a convex emitting surface 621 as shown in FIG. 5B), and that provides one, more or all of the herein described advantages. The energy output of the inventive handpiece can, consequently, provide, for example, a desired beam distribution (e.g., with the beam focus point or the peak concentration of the beam) at the cutting area. The cutting area can be spaced, for example, about 4 to about 10 mm, or, in particular and/or preferred examples, about 5 to about 7 mm, from the emitting surface. All three optical elements can be designed, in various combinations, to provide the desired beam distribution (e.g., a beam focus and/or a peak concentration of the beam) at the predetermined distances.

In a typical implementation of the invention, such as illustrated in FIG. 5A or 5B, the output tip 520/620 is first constructed to have an output surface 521/621 in a shape of, and/or with the functionality of, a lens, and, subsequently, one or more of other surfaces (e.g., five surfaces including output end of trunk fiber, i.e., waveguide 505/605, surfaces of window 510/610 and reflector 515/615, and input 519/619 of tip 520/620), are designed to possess, e.g., one or more of a flat and a curved surface.

One of possible combinations is to keep the window 510 not changed, make the reflector 515 (e.g., 90-degree mirror) flat and add convex surfaces 519 and 521 to both ends of the output tip 520 (FIG. 5A). These choices may allow creating a beam waist having a diameter nearly the same as the diameter of the original fiber, i.e., waveguide 505, at a certain (e.g., predefined, e.g., 5, 6 or 7 mm) distance away from the tip surface. In addition, that implementation may allow maintenance of a relatively high power density (e.g., and/or of no, or no significant, variation) at the certain distance (e.g., around the beam waist).

According to one feature of the present invention, the output tip is interchangeable to allow switching between different output tips for functionality variation (e.g., of a converging characteristic performed on the beam, such as a change of the selected distance where the "waist" occurs and/or the width and/or cross-sectional shape and/or power density of the waist) and/or for cleaning/autoclaving. It is an advantage and difference compared to prior art (with protective window).

Figure 6:
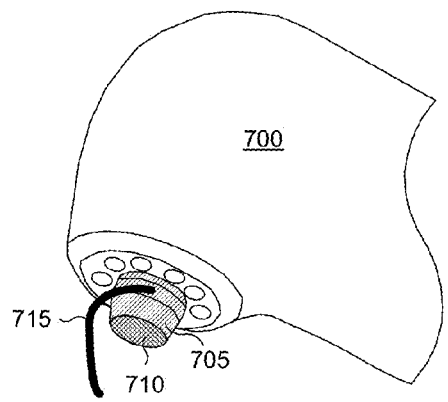
FIG. 6 is a pictorial diagram of an embodiment of a laser handpiece incorporating a beam guide.

According to another feature as illustrated in FIG. 6, as the tip is non-contact and works at a certain (e.g., predetermined) distance above the tissue, an embodiment of the laser handpiece may be formed to include an (optional) "beam guide" 715, which may be affixed to a housing 705 that supports a tip (not shown) within tip ferrule 710 (cf. tip ferrule of FIG. 1) of a handpiece 700. The beam guide or reference arm added to the design may comprise a straight, curved, spiral, or any other shape or shapes (e.g., of an elongate member or members) for facilitating spacing of the tip 710 from the tissue. The beam guide feature(s) may provide a visible and "feelable" reference to the location of the cutting area of the laser beam and/or a bottom of a cavity created by the cutting.

The electromagnetic energy emitted by the handpiece may comprise laser energy and/or visible light and may operate to provide or promote one or more of cutting, ablating, desterilization, bacterial reduction, biostimulation (e.g., low-level light therapy), coagulation, remodeling, caries detection or treatment, and illumination (e.g., with visible light).

In certain implementations, the electromagnetic energy can comprise one or more of an electromagnetic energy source of ablation, and/or an electromagnetic energy source of illumination, and/or an electromagnetic energy source of tissue disruption, and/or an electromagnetic energy source of biostimulation.

The target surface may comprise, for example, one or more of tooth tissue, bone, cartilage and soft tissue such as skin or nasal-cavity tissue.

According to certain aspects of the present invention, the energy output can comprise one or more of hard-tissue ablating electromagnetic energy, low-level light therapy (LLLT) electromagnetic energy, tissue-biostimulation electromagnetic energy, visible electromagnetic energy, coherent light, one or more of a wavelength within a range from about 2.69 to about 2.80 microns and a wavelength of about 2.94 microns, and electromagnetic energy generated by one or more of an Er:YAG laser, an Er:YSGG laser, an Er, a Cr:YSGG laser and a CTE:YAG laser.

In one implementation, a structure (e.g., cannula(s) or orifice(s)) can be configured to direct liquid in a direction toward the distal end of the output tip. For example, a fluid can be routed distally along an outer surface (e.g., the entire or substantially the entire outer surface, near the distal end) of the output tip.

In another implementation, fluid may be supplied through one or more gaps disposed between an outer surface of the waveguide (e.g., fiber optic) and the interior surface of a cannula. The fluid can be a liquid or may comprise a combination of liquid and gas. In certain implementations, the liquid is or comprises water, and in other implementations it is or comprises both air and water which, for example, can be mixed together either before or within the gap. For example, the fluid can comprise atomized fluid particles formed from a mixture of pressurized air and water and delivered through the gap to exit from the fluid output.

A volume between the tissue ablating and/or tissue-treating distal end and the distal end of a cannula (e.g., holding the output tip and one, more, or all of the other operating components of the handpiece, in which case the handpiece is not a handpiece but rather is an intra-luminal, lipo, or joint surgery device) can be transparent to a wavelength of energy emitted from the source of electromagnetic energy. According to another implementation, in addition to or as an alternative to the preceding features, a volume between (a) the tissue ablating and/or tissue-treating distal end and (b) the distal end of the cannula does not obstruct atomized fluid particles traveling in the direction from the fluid output to the distal end of the cannula. According to yet another implementation, in addition to or as an alternative to any one or more features set forth in this paragraph, a volume between (a) the tissue ablating and/or tissue-treating distal end and (b) the target surface is not obstructed by any part of the apparatus.

According to other implementations, the apparatus can comprise a fluid output that is configured to emit fluid in a vicinity of the distal end of the apparatus, wherein: the fluid output comprises an atomizer configured to place atomized fluid particles into a volume above the target surface. Further, the electromagnetic energy waveguide is configured to impart relatively large amounts of energy into the atomized fluid particles in the volume above the target surface to thereby expand the atomized fluid particles and impart disruptive forces onto the target surface.

According to another aspect of the present invention, a medical handpiece includes a handpiece housing and a source of electromagnetic energy disposed within the handpiece housing and adapted for emitting electromagnetic energy from a distal end of the handpiece housing. An illumination source is disposed within the handpiece housing for projecting light from the distal end of the handpiece housing onto a target surface. The illumination source may include a fiber optic bundle. A medication line may also be disposed within the handpiece housing for outputting medication through a distal end of the handpiece housing onto a target surface.

According to certain implementations, laser energy from the trunk fiber is output from a power or treatment fiber, and is directed, for example, into fluid (e.g., an air and/or water spray or an atomized distribution of fluid particles from a water connection and/or a spray connection near an output end of a handpiece) that is emitted from a fluid output of a handpiece above a target surface (e.g., one or more of tooth, bone, cartilage and soft tissue). The fluid output may comprise a plurality of fluid outputs, concentrically arranged around a power fiber, as described in, for example, application Ser. No. 11/042,824 and Prov. App. 60/601,415. The power or treatment fiber may be coupled to an electromagnetic energy source comprising one or more of a wavelength within a range from about 2.69 to about 2.80 microns and a wavelength of about 2.94 microns. In certain implementations the power fiber may be coupled to one or more of an Er:YAG laser, an Er:YSGG laser, an Er, Cr:YSGG laser and a CTE:YAG laser, and in particular instances may be coupled to one of an Er, Cr:YSGG solid state laser having a wavelength of about 2.789 microns and an Er:YAG solid state laser having a wavelength of about 2.940 microns. An apparatus including corresponding structure for directing electromagnetic energy into an atomized distribution of fluid particles above a target surface is disclosed, for example, in the below-referenced U.S. Pat. No. 5,574,247, which describes the impartation of laser energy into fluid particles to thereby apply disruptive forces to the target surface.

By way of the disclosure herein, a laser assembly has been described that can output electromagnetic radiation useful to diagnose, monitor and/or affect a target surface. In the case of procedures using fiber optic tip radiation, a probe can include one or more power or treatment fibers for transmitting treatment radiation to a target surface for treating (e.g., ablating) a dental structure, such as within a canal. In any of the embodiments described herein, the light for illumination and/or diagnostics may be transmitted simultaneously with, or intermittently with or separate from, transmission of treatment radiation and/or of the fluid from the fluid output or outputs.

Corresponding or related structure and methods described in the following patents assigned to Biolase Technology, Inc. are incorporated herein by reference in their entireties, wherein such incorporation includes corresponding or related structure (and modifications thereof) in the following patents which may be, in whole or in part, (i) operable with, (ii) modified by one skilled in the art to be operable with, and/or (iii) implemented/used with or in combination with, any part (s) of the present invention according to this disclosure, that of the patents or below applications, and the knowledge and judgment of one skilled in the art.

Such patents include, but are not limited to U.S. Pat. No. 7,578,622 entitled Contra-angle rotating handpiece having tactile-feedback tip ferrule; U.S. Pat. No. 7,575,381 entitled Fiber tip detector apparatus and related methods; U.S. Pat. No. 7,563,226 entitled Handpieces having illumination and laser outputs; U.S. Pat. No. 7,467,946 entitled Electromagnetic radiation emitting toothbrush and dentifrice system; U.S. Pat. No. 7,461,982 entitled Contra-angle rotating handpiece having tactile-feedback tip ferrule; U.S. Pat. No. 7,461,658 entitled Methods for treating eye conditions; U.S. Pat. No. 7,458,380 entitled Methods for treating eye conditions; U.S. Pat. No. 7,424,199 entitled Fiber tip fluid output device; U.S. Pat. No. 7,421,186 entitled Modified-output fiber optic tips; U.S. Pat. No. 7,415,050 entitled Electromagnetic energy distributions for electromagnetically induced mechanical cutting; U.S. Pat. No. 7,384,419 entitled Tapered fused waveguide for delivering treatment electromagnetic radiation toward a target surface; U.S. Pat. No. 7,356,208 entitled Fiber detector apparatus and related methods; U.S. Pat. No. 7,320,594 entitled Fluid and laser system; U.S. Pat. No. 7,303,397 entitled Caries detection using timing differentials between excitation and return pulses; U.S. Pat. No. 7,292,759 entitled Contra-angle rotating handpiece having tactile-feedback tip ferrule; U.S. Pat. No. 7,290,940 entitled Fiber tip detector apparatus and related methods; U.S. Pat. No. 7,288,086 entitled High-efficiency, side-pumped diode laser system; U.S. Pat. No. 7,270,657 entitled Radiation emitting apparatus with spatially controllable output energy distributions; U.S. Pat. No. 7,261,558 entitled Electromagnetic radiation emitting toothbrush and dentifrice system; U.S. Pat. No. 7,194,180 entitled Fiber detector apparatus and related methods; U.S. Pat. No. 7,187,822 entitled Fiber tip fluid output device; U.S. Pat. No. 7,144,249 entitled Device for dental care and whitening; U.S. Pat. No. 7,108,693 entitled Electromagnetic energy distributions for electromagnetically induced mechanical cutting; U.S. Pat. No. 7,068,912 entitled Fiber detector apparatus and related methods; U.S. Pat. No. 6,942,658 entitled Radiation emitting apparatus with spatially controllable output energy distributions; U.S. Pat. No. 6,829,427 entitled Fiber detector apparatus and related methods; U.S. Pat. No. 6,821,272 entitled Electromagnetic energy distributions for electromagnetically induced cutting; U.S. Pat. No. 6,744,790 entitled Device for reduction of thermal lensing; U.S. Pat. No. 6,669,685 entitled Tissue remover and method; U.S. Pat. No. 6,616,451 entitled Electromagnetic radiation emitting toothbrush and dentifrice system; U.S. Pat. No. 6,616,447 entitled Device for dental care and whitening; U.S. Pat. No. 6,610,053 entitled Methods of using atomized particles for electromagnetically induced cutting; U.S. Pat. No. 6,567,582 entitled Fiber tip fluid output device; U.S. Pat. No. 6,561,803 entitled Fluid conditioning system; U.S. Pat. No. 6,544,256 entitled Electromagnetically induced cutting with atomized fluid particles for dermatological applications; U.S.

Pat. No. 6,533,775 entitled Light-activated hair treatment and removal device; U.S. Pat. No. 6,389,193 entitled Rotating handpiece; U.S. Pat. No. 6,350,123 entitled Fluid conditioning system; U.S. Pat. No. 6,288,499 entitled Electromagnetic energy distributions for electromagnetically induced mechanical cutting; U.S. Pat. No. 6,254,597 entitled Tissue remover and method; U.S. Pat. No. 6,231,567 entitled Material remover and method; U.S. Pat. No. 6,086,367 entitled Dental and medical procedures employing laser radiation; U.S. Pat. No. 5,968,037 entitled User programmable combination of atomized particles for electromagnetically induced cutting; U.S. Pat. No. 5,785,521 entitled Fluid conditioning system; and U.S. Pat. No. 5,741,247 entitled Atomized fluid particles for electromagnetically induced cutting.

Also, the above disclosure and referenced items, and that described on the referenced pages, are intended to be operable or modifiable to be operable, in whole or in part, with corresponding or related structure and methods, in whole or in part, described in the following published applications and items referenced therein, which applications are listed as follows: App. Pub. 20090225060 entitled Wrist-mounted laser with animated, page-based graphical user-interface; App. Pub. 20090143775 entitled Medical laser having controlled-temperature and sterilized fluid output; App. Pub. 20090141752 entitled Dual pulse-width medical laser with presets; App. Pub. 20090105707 entitled Drill and flavored fluid particles combination; App. Pub. 20090104580 entitled Fluid and pulsed energy output system; App. Pub. 20090076490 entitled Fiber tip fluid output device; App. Pub. 20090075229 entitled Probes and biofluids for treating and removing deposits from tissue surfaces; App. Pub. 20090067189 entitled Contra-angle rotating handpiece having tactile-feedback tip ferrule; App. Pub. 20090062779 entitled Methods for treating eye conditions with low-level light therapy; App. Pub. 20090056044 entitled Electromagnetic radiation emitting toothbrush and dentifrice system; App. Pub. 20090043364 entitled Electromagnetic energy distributions for Electromagnetically induced mechanical cutting; App. Pub. 20090042171 entitled Fluid controllable laser endodontic cleaning and disinfecting system; App. Pub. 20090035717 entitled Electromagnetic radiation emitting toothbrush and transparent dentifrice system; App. Pub. 20090031515 entitled Transparent dentifrice for use with electromagnetic radiation emitting toothbrush system; App. Pub. 20080317429 entitled Modified-output fiber optic tips; App. Pub. 20080276192 entitled Method and apparatus for controlling an electromagnetic energy output system; App. Pub. 20080240172 entitled Radiation emitting apparatus with spatially controllable output energy distributions; App. Pub. 20080221558 entitled Multiple fiber-type tissue treatment device and related method; App. Pub. 20080219629 entitled Modified-output fiber optic tips; App. Pub. 20080212624 entitled Dual pulse-width medical laser; App. Pub. 20080203280 entitled Target-close electromagnetic energy emitting device; App. Pub. 20080181278 entitled Electromagnetic energy output system; App. Pub. 20080181261 entitled Electromagnetic energy output system; App. Pub. 20080157690 entitled Electromagnetic energy distributions for electromagnetically induced mechanical cutting; App. Pub. 20080151953 entitled Electromagnet energy distributions for electromagnetically induced mechanical cutting; App. Pub. 20080138764 entitled Fluid and laser system; App. Pub. 20080125677 entitled Methods for treating hyperopia and presbyopia via laser tunneling; App. Pub. 20080125676 entitled Methods for treating hyperopia and presbyopia via laser tunneling; App. Pub. 20080097418 entitled Methods for treating eye conditions; App. Pub. 20080097417 entitled Methods for treating eye conditions; App. Pub. 20080097416 entitled Methods for treating eye conditions; App. Pub. 20080070185 entitled Caries detection using timing differentials between excitation and return pulses; App. Pub. 20080069172 entitled Electromagnetic energy distributions for electromagnetically induced mechanical cutting; App. Pub. 20080065057 entitled High-efficiency, side-pumped diode laser system; App. Pub. 20080065055 entitled Methods for treating eye conditions; App. Pub. 20080065054 entitled Methods for treating hyperopia and presbyopia via laser tunneling; App. Pub. 20080065053 entitled Methods for treating eye conditions; App. Pub. 20080033411 entitled High efficiency electromagnetic laser energy cutting device; App. Pub. 20080033409 entitled Methods for treating eye conditions; App. Pub. 20080033407 entitled Methods for treating eye conditions; App. Pub. 20080025675 entitled Fiber tip detector apparatus and related methods; App. Pub. 20080025672 entitled Contra-angle rotating handpiece having tactile-feedback tip ferrule; App. Pub. 20080025671 entitled Contra-angle rotating handpiece having tactile-feedback tip ferrule; App. Pub. 20070298369 entitled Electromagnetic radiation emitting toothbrush and dentifrice system; App. Pub. 20070263975 entitled Modified-output fiber optic tips; App. Pub. 20070258693 entitled Fiber detector apparatus and related methods; App. Pub. 20070208404 entitled Tissue treatment device and method; App. Pub. 20070208328 entitled Contra-angel rotating handpiece having tactile-feedback tip ferrule; App. Pub. 20070190482 entitled Fluid conditioning system; App. Pub. 20070184402 entitled Caries detection using real-time imaging and multiple excitation frequencies; App. Pub. 20070128576 entitled Output attachments coded for use with electromagnetic-energy procedural device; App. Pub. 20070104419 entitled Fiber tip fluid output device; App. Pub. 20070060917 entitled High-efficiency, side-pumped diode laser system; App. Pub. 20070059660 entitled Device for dental care and whitening; App. Pub. 20070054236 entitled Device for dental care and whitening; App. Pub. 20070054235 entitled Device for dental care and whitening; App. Pub. 20070054233 entitled Device for dental care and whitening; App. Pub. 20070042315 entitled Visual feedback implements for electromagnetic energy output devices; App. Pub. 20070016176 entitled Laser handpiece architecture and methods; App. Pub. 20070014517 entitled Electromagnetic energy emitting device with increased spot size; App. Pub. 20070014322 entitled Electromagnetic energy distributions for electromagnetically induced mechanical cutting; App. Pub. 20070009856 entitled Device having activated textured surfaces for treating oral tissue; App. Pub. 20070003604 entitled Tissue coverings bearing customized tissue images; App. Pub. 20060281042 entitled Electromagnetic radiation emitting toothbrush and dentifrice system; App. Pub. 20060275016 entitled Contra-angle rotating handpiece having tactile-feedback tip ferrule; App. Pub. 20060241574 entitled Electromagnetic energy distributions for electromagnetically induced disruptive cutting; App. Pub. 20060240381 entitled Fluid conditioning system; App. Pub. 20060210228 entitled Fiber detector apparatus and related methods; App. Pub. 20060204203 entitled Radiation emitting apparatus with spatially controllable output energy distributions; App. Pub. 20060142745 entitled Dual pulse-width medical laser with presets; App. Pub. 20060142744 entitled Identification connector for a medical laser handpiece; App. Pub. 20060142743 entitled Medical laser having controlled-temperature and sterilized fluid output; App. Pub. 20060126680 entitled Dual pulse-width medical laser; App. Pub. 20060099548 entitled Caries detection using timing differentials between excitation and return pulses; App. Pub.

20060083466 entitled Fiber tip detector apparatus and related methods; App. Pub. 20060043903 entitled Electromagnetic energy distributions for electromagnetically induced mechanical cutting; App. Pub. 20050283143 entitled Tissue remover and method; App. Pub. 20050281887 entitled Fluid conditioning system; App. Pub. 20050281530 entitled Modified-output fiber optic tips; App. Pub. 20050256517 entitled Electromagnetically induced treatment devices and methods; App. Pub. 20050256516 entitled Illumination device and related methods; App. Pub. 20040106082 entitled Device for dental care and whitening; App. Pub. 20040092925 entitled Methods of using atomized particles for electromagnetically induced cutting; App. Pub. 20040091834 entitled Electromagnetic radiation emitting toothbrush and dentifrice system; App. Pub. 20040068256 entitled Tissue remover and method; App. Pub. 20030228094 entitled Fiber tip fluid output device; App. Pub. 20020149324 entitled Electromagnetic energy distributions for electromagnetically induced mechanical cutting; and App. Pub. 20020014855 entitled Electromagnetic energy distributions for electromagnetically induced mechanical cutting.

All of the contents of the preceding applications are incorporated herein by reference in their entireties. Although the disclosure herein refers to certain illustrated embodiments, it is to be understood that these embodiments have been presented by way of example rather than limitation. For example, any of the radiation outputs (e.g., lasers), any of the fluid outputs (e.g., water outputs), and any conditioning agents, particles, agents, etc., and particulars or features thereof, or other features, including method steps and techniques, may be used with any other structure(s) and process described or referenced herein, in whole or in part, in any combination or permutation as a non-equivalent, separate, non-interchangeable aspect of this invention. Corresponding or related structure and methods specifically contemplated, disclosed and claimed herein as part of this invention, to the extent not mutually inconsistent as will be apparent from the context, this specification, and the knowledge of one skilled in the art, including, modifications thereto, which may be, in whole or in part, (i) operable and/or constructed with, (ii) modified by one skilled in the art to be operable and/or constructed with, and/or (iii) implemented/made/used with or in combination with, any parts of the present invention according to this disclosure, include: (I) any one or more parts of the above disclosed or referenced structure and methods and/or (II) subject matter of any one or more of the following claims and parts thereof, in any permutation and/or combination. The intent accompanying this disclosure is to have such embodiments construed in conjunction with the knowledge of one skilled in the art to cover all modifications, variations, combinations, permutations, omissions, substitutions, alternatives, and equivalents of the embodiments, to the extent not mutually exclusive, as may fall within the spirit and scope of the invention as limited only by the appended claims.

What is claimed is:

1. A handpiece for laser treating a tissue target surface, comprising:
    a housing;
    a waveguide extending within the housing;
    a window supported by the housing and coupled to receive and output an electromagnetic energy from the waveguide:
    a reflector supported by the housing and aligned to redirect the electromagnetic energy outputted from the window;
    a tip supported by the housing in a position to receive the electromagnetic energy from the reflector d shaped to generate an output of the electromagnetic energy that converges to a predefined configuration at a predefined distance from an emitting surface of the tip: and
    a beam guide projecting from the housing a reference distance that locates the emitting surface of the tip at the predefined distance from the tissue target surface when the beam guide contacts the tissue target surface, whereby the beam guide can ensure that the output of the electromagnetic energy will have the predefined configuration at the tissue target surface.

2. The handpiece as set forth in claim 1, wherein the electromagnetic energy directed to the tissue target surface is focused at the predefined distance.

3. The handpiece as set forth in claim 1, wherein the predefined distance ranges from about 5 mm to about 10 mm.

4. The handpiece as set forth in claim 1, further comprising a fluid output supported by the housing and adapted to emit fluid particles, whereby the electromagnetic energy emitted from the tip imparts energy into the fluid particles to thereby apply disruptive forces to the tissue target surface.

5. The handpiece as set forth in claim 1, further comprising a plurality of output tips having different beam-converging characteristics, wherein the tip comprises an output tip that is interchangeable with the other output tips.

6. The handpiece as set forth in claim 1, wherein the beam guide comprises an elongate member with an outer end spaced the reference distance from the housing.

7. The handpiece as set forth in claim 6, wherein the beam guide is straight between the housing and the outer end.

8. The handpiece as set forth in claim 6, wherein the beam guide is curved between the housing and the outer end.

9. The handpiece as set forth in claim 6, wherein the beam guide is spiral between the housing and the outer end.

* * * * *